United States Patent
Lamkin et al.

(10) Patent No.: US 9,482,301 B2
(45) Date of Patent: Nov. 1, 2016

(54) BRAKE DISC STACK WEAR MEASUREMENT

(71) Applicant: Honeywell International Inc., Morristown, NJ (US)

(72) Inventors: Andrew Fannon Lamkin, Albuquerque, NM (US); Christopher Montano, Rio Rancho, NM (US); PerriLynne Silva, Rio Rancho, NM (US)

(73) Assignee: Honeywell International Inc., Morris Plains, NJ (US)

( * ) Notice: Subject to any disclaimer, the term of this patent is extended or adjusted under 35 U.S.C. 154(b) by 0 days.

(21) Appl. No.: 14/668,392

(22) Filed: Mar. 25, 2015

(65) Prior Publication Data
US 2016/0281808 A1    Sep. 29, 2016

(51) Int. Cl.
| | |
|---|---|
| *F16D 66/02* | (2006.01) |
| *F16D 65/52* | (2006.01) |
| *F16D 55/38* | (2006.01) |
| *G01N 27/72* | (2006.01) |

(52) U.S. Cl.
CPC ............. *F16D 66/024* (2013.01); *F16D 55/38* (2013.01); *F16D 65/52* (2013.01); *G01N 27/72* (2013.01)

(58) Field of Classification Search
CPC ...... F16D 66/02; F16D 66/024; F16D 65/52; F16D 55/38
USPC ........................................ 188/1.11 W, 1.11 L
See application file for complete search history.

(56) References Cited

U.S. PATENT DOCUMENTS

| | | |
|---|---|---|
| 2,522,181 A | 9/1950 | Krikorian |
| 3,604,865 A | 9/1971 | Bricker |
| 4,013,143 A | 3/1977 | Juhasz |
| 4,107,604 A | 8/1978 | Bernier |
| 4,184,145 A | 1/1980 | Fima |
| 4,279,214 A | 7/1981 | Thorn |
| 4,495,464 A | 1/1985 | Kozai et al. |
| 4,520,661 A | 6/1985 | Tamai et al. |
| 4,550,815 A | 11/1985 | Gale |
| 4,583,071 A | 4/1986 | Sebalos et al. |
| 4,642,603 A | 2/1987 | Martinez, Jr. |

(Continued)

FOREIGN PATENT DOCUMENTS

| | | |
|---|---|---|
| DE | 3220773 A1 | 12/1983 |
| DE | 102005013142 A1 | 9/2006 |

(Continued)

OTHER PUBLICATIONS

Extended European Search Report from counterpart European Application No. 16159532.7-1756, dated Aug. 22, 2016, 9 pp.

*Primary Examiner* — Melanie Torres Williams
(74) *Attorney, Agent, or Firm* — Shumaker & Sieffert, P.A.

(57) ABSTRACT

In some examples, a brake wear measurement system includes an emitter configured to emit a signal and a passive powered sensor system including a controller and a sensor configured to sense the signal emitted by the emitter. The emitter and the sensor of the sensor system are mounted on the brake assembly such as the emitter and the sensor may be configured to move relative to each other as the brake disc stack wears. Thus, a characteristic of the signal emitted by the emitter and sensed by the sensor may change as a function of the brake disc stack wear. The brake wear measurement may further include a processor configured to receive the output generated by the sensor and determine, based on the output, an amount of wear of the brake disc stack assembly.

20 Claims, 5 Drawing Sheets

(56) References Cited

U.S. PATENT DOCUMENTS

| | | | |
|---|---|---|---|
| 4,664,239 A | 5/1987 | Symes et al. | |
| 4,757,300 A | 7/1988 | Sebalos | |
| 4,776,438 A | 10/1988 | Schandelmeier | |
| 4,852,404 A | 8/1989 | Catanese | |
| 4,855,712 A | 8/1989 | Wiley, Jr. et al. | |
| 4,989,537 A | 2/1991 | Hutchinson, Sr. et al. | |
| 5,035,303 A | 7/1991 | Sullivan | |
| 5,044,302 A | 9/1991 | Goldfein et al. | |
| 5,087,907 A | 2/1992 | Weiler et al. | |
| 5,125,280 A | 6/1992 | Koscinski et al. | |
| 5,148,107 A | 9/1992 | Finger et al. | |
| 5,186,284 A * | 2/1993 | Lamela | F16D 55/36 188/1.11 R |
| 5,228,541 A | 7/1993 | Plude | |
| 5,251,729 A | 10/1993 | Nehl et al. | |
| 5,255,760 A | 10/1993 | Lamb et al. | |
| 5,255,761 A | 10/1993 | Zaremsky | |
| 5,310,023 A | 5/1994 | Martinez | |
| 5,327,782 A | 7/1994 | Sato et al. | |
| 5,410,293 A | 4/1995 | Angerfors | |
| 5,433,296 A | 7/1995 | Webberley | |
| 5,450,930 A | 9/1995 | Martens et al. | |
| 5,474,154 A | 12/1995 | Coale | |
| 5,494,138 A | 2/1996 | Scelsi et al. | |
| 5,717,174 A | 2/1998 | Ramos | |
| 5,767,768 A | 6/1998 | DiSaverio | |
| 5,825,287 A | 10/1998 | Zarybnicky, Sr. et al. | |
| 5,848,672 A | 12/1998 | Brearley et al. | |
| 5,906,253 A | 5/1999 | Rancourt et al. | |
| 5,934,415 A | 8/1999 | Preston et al. | |
| 5,967,266 A | 10/1999 | Carnegie | |
| 6,003,640 A | 12/1999 | Ralea | |
| 6,112,859 A | 9/2000 | Shuck et al. | |
| 6,202,811 B1 | 3/2001 | Wallrafen | |
| 6,237,723 B1 | 5/2001 | Salsman | |
| 6,257,374 B1 | 7/2001 | Strzelczyk et al. | |
| 6,328,144 B1 | 12/2001 | Hayakawa et al. | |
| 6,352,137 B1 | 3/2002 | Stegall et al. | |
| 6,356,072 B1 | 3/2002 | Chass | |
| 6,411,206 B1 | 6/2002 | Weant et al. | |
| 6,460,659 B1 | 10/2002 | Schaffer et al. | |
| 6,634,465 B1 | 10/2003 | Tuschen | |
| 6,659,233 B2 * | 12/2003 | DeVlieg | B60T 8/1703 188/1.11 E |
| 6,696,937 B1 | 2/2004 | Kiefer | |
| 6,702,069 B2 | 3/2004 | Ralea et al. | |
| 6,719,102 B2 | 4/2004 | Takanashi | |
| 6,753,771 B2 | 6/2004 | Lesesky | |
| 6,776,266 B2 | 8/2004 | Fuglewicz et al. | |
| 6,929,333 B2 | 8/2005 | DeVlieg | |
| 7,014,016 B2 | 3/2006 | Morris et al. | |
| 7,086,503 B2 | 8/2006 | Miller et al. | |
| 7,108,107 B2 | 9/2006 | Ralea et al. | |
| 7,114,596 B2 | 10/2006 | Borugian | |
| 7,322,447 B2 | 1/2008 | Deckhut et al. | |
| 7,525,062 B2 | 4/2009 | Adam et al. | |
| 7,535,131 B1 | 5/2009 | Safieh, Jr. | |
| 7,610,998 B2 | 11/2009 | Baumgartner et al. | |
| 7,673,721 B2 | 3/2010 | Bailey et al. | |
| 7,766,130 B2 | 8/2010 | Walker et al. | |
| 7,877,216 B2 | 1/2011 | Wright et al. | |
| 8,207,729 B2 | 6/2012 | Erickson et al. | |
| 8,717,159 B2 | 5/2014 | Todd et al. | |
| 2004/0251090 A1 | 12/2004 | Morris et al. | |
| 2005/0269873 A1 | 12/2005 | DeVlieg | |
| 2006/0042734 A1 | 3/2006 | Turner et al. | |
| 2006/0108182 A1 | 5/2006 | Walker et al. | |
| 2006/0191751 A1 | 8/2006 | Miller et al. | |
| 2006/0219487 A1 | 10/2006 | Wille et al. | |
| 2006/0232392 A1 | 10/2006 | Emmett et al. | |
| 2007/0125607 A1 | 6/2007 | Ralea et al. | |
| 2008/0073161 A1 | 3/2008 | Pettersson et al. | |
| 2008/0190712 A1 | 8/2008 | Hagberg | |
| 2008/0202865 A1 | 8/2008 | Pradier et al. | |
| 2009/0050418 A1 | 2/2009 | Vargas et al. | |
| 2009/0120735 A1 | 5/2009 | DeVlieg | |
| 2009/0177362 A1 | 7/2009 | Schmitt et al. | |
| 2009/0205910 A1 | 8/2009 | Cahill | |
| 2009/0229926 A1 | 9/2009 | Schaefer | |
| 2010/0286881 A1 | 11/2010 | Cahill | |
| 2012/0226457 A1 | 9/2012 | Erickson et al. | |

FOREIGN PATENT DOCUMENTS

| | | |
|---|---|---|
| EP | 1538364 A1 | 6/2005 |
| FR | 2874675 A1 | 3/2006 |
| GB | 2302574 A | 1/1997 |
| GB | 2386951 | 10/2003 |
| GB | 2470098 | 11/2010 |
| JP | 2013088196 | 5/2013 |
| WO | 2004106766 A1 | 12/2004 |

* cited by examiner

BRAKE DISC STACK WEAR MEASUREMENT

TECHNICAL FIELD

This disclosure relates to vehicle braking systems, such as an aircraft braking assembly.

BACKGROUND

A brake assembly of an aircraft or another vehicle has a limited useable life, as determined through wear, and may have an associated operating and maintenance cost that is based on the actual use of the brake assembly and how fast the life of the brake assembly is consumed. As a result of varying external factors and varying frictional forces during braking events, different brake assemblies may experience different rates of wear over time.

SUMMARY

Devices, systems, and techniques for determining an amount of wear of a brake disc stack of a brake assembly, such as an aircraft brake assembly, are described herein. In some examples, a brake wear measurement system includes an emitter configured to emit a signal and a passive powered sensor system including a controller and a sensor configured to sense the signal emitted by the emitter. In some examples, the emitter includes a magnetic field emitter and the sensor includes a magnetic field strength sensor. The emitter and the sensor of the sensor system are mounted on the brake assembly such as the emitter and the sensor may be configured to move relative to each other as the brake disc stack wears. Thus, a characteristic of the signal emitted by the emitter and sensed by the sensor may change as a function of the brake disc stack wear. The brake wear measurement may further include a processor configured to receive the output generated by the sensor and determine, based on the output, an amount of wear of the brake disc stack assembly. The amount of wear (or "level" of wear) can be, for example, a percentage of useful life of the brake disc stack remaining, a magnitude of wear (e.g., as measured in units of length), or any other suitable quantification of the amount of wear. In some examples, the processor may reference a data structure that associates sensor outputs with the amount of brake disc stack wear in order to determine the amount of wear indicated by a particular sensor output.

In one example, the disclosure is directed to a system comprising a brake disc stack and an emitter configured to emit a signal. The system further includes a sensor configured to sense the emitted signal, generate an output indicative of a characteristic of the sensed signal, wherein the sensor and the emitter are configured to move relative to each other as the brake disk stack wears. The system further includes a passively powered controller operatively coupled to the sensor and configured to wirelessly receive power from a remote device, receive the output generated by the sensor, and a processor configured to determine an amount of wear of the brake disc stack based on the output generated by the sensor. The controller may be configured to transmit, to the remote device, at least one of: information indicative of the output generated by the sensor or the amount of wear of the brake disc stack determined based on the output.

In another example, the disclosure is directed to a method comprising emitting, by an emitter, a signal, and detecting, by a sensor, the signal emitted by the emitter. The method includes generating, by the sensor, an output indicative of a characteristic of the signal emitted by the emitter, and wirelessly receiving, by a passively powered controller, power from a remote device. The method further includes receiving, by the passively powered controller, the output generated by the sensor, and determining an amount of wear of a brake disc stack based on the output generated by the sensor.

In another example, the disclosure is directed to a system comprising means means for emitting, by an emitter, a signal, and means for detecting, by a sensor, the signal emitted by the emitter. The system includes means for generating, by the sensor, an output indicative of a characteristic of the signal emitted by the emitter, and means for wirelessly receiving, by a passively powered controller, power from a remote device. The system further includes means for receiving, by the passively powered controller, the output generated by the sensor, and means for determining an amount of wear of a brake disc stack based on the output generated by the sensor.

The disclosure is also directed to an article of manufacture comprising a computer-readable storage medium. The computer-readable storage medium comprises computer-readable instructions that are executable by a processor. The instructions cause the processor to perform any part of the techniques described herein. The instructions may be, for example, software instructions, such as those used to define a software or computer program. The computer-readable medium may be a computer-readable storage medium such as a storage device (e.g., a disk drive, or an optical drive), memory (e.g., a Flash memory, read only memory (ROM), or random access memory (RAM)) or any other type of volatile or non-volatile memory or storage element that stores instructions (e.g., in the form of a computer program or other executable) to cause a processor to perform the techniques described herein. The computer-readable medium may be a non-transitory storage medium.

The details of one or more examples are set forth in the accompanying drawings and the description below. Other features, objects, and advantages of the disclosure will be apparent from the description and drawings, and from the claims.

DETAILED DESCRIPTION

Figure 1:
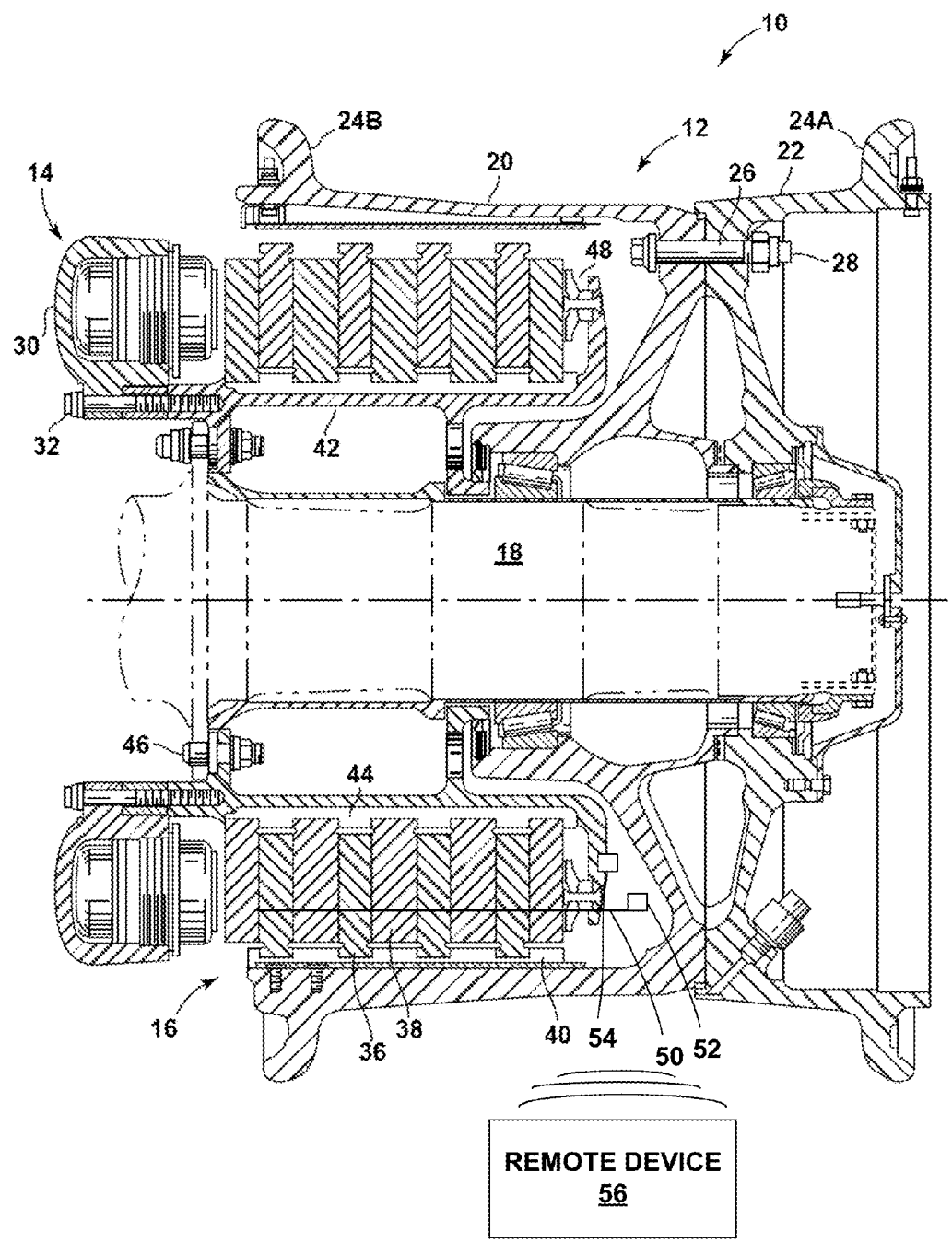
FIG. 1 is a schematic diagram illustrating an example aircraft brake assembly and an example wear measurement system.

Example devices, systems, and techniques for determining an amount of wear of a brake disc stack of a brake assembly are described herein. In some examples, a brake wear measurement system includes an emitter and a passive powered sensor system including a controller and a sensor. The emitter and at least the sensor of the sensor system are mounted on the brake assembly such the emitter and sensor may be configured to move relative to each other as the brake disc stack wears. For example, one of the emitter or the sensor may be mounted on a bracket and may remain stationary as the brake disc stack wears, and the other of the emitter or the sensor may be configured to move with the brake disc stack as it wears (e.g., on a wear pin or a pressure plate of the brake disc stack).

The emitter and the sensor may not be electrically coupled to each other via wire. In some examples, as the emitter and the sensor move towards or away from each other as the brake disc stack wears, a characteristic of the signal emitted by the emitter and sensed by the sensor may change as a function of the brake disc stack wear. A processor may receive, from the sensor assembly, an indication of the characteristic of the signal sensed by the sensor and determine an amount of brake disc stack wear based on the characteristic of the signal sensed by the sensor. For example, the emitter may include a magnet that emits a magnetic field, and different levels of brake disc stack wear may be associated with different magnetic field characteristics, e.g., in a mapping table or other data structure, and the processor may compare the received magnetic field characteristic to the data structure to determine the brake disc stack wear. As an example, the magnetic field characteristics may be associated with values corresponding to a distance between the field emitter and the sensor, which may change as a function of the amount of brake disc stack wear. The processor can be a part of the sensor assembly mounted on the aircraft brake assembly or can be part of a remote device, separate from and not wired to the sensor assembly.

The emitter, the sensor system, or both the emitter and sensor system may be passively powered. For example, rather than including a power source, the sensor system may be passively powered by the remote device. The remote device may emit energy (e.g., electromagnetic waves) that powers the sensor system, and, in response to being powered, the sensor system may transmit an indication of a characteristic of the signal sensed by the sensor or an amount of brake disc wear determined based on the characteristic of the signal sensed by the sensor. Likewise, in some examples, if the emitter requires power, the emitter may be powered by the remote device. In some examples, the remote device receives the indication of the characteristic of the signal and determines the amount of brake disc stack wear based on the received indication.

The passive powering of the sensor system, as well as the wireless data path between the sensor system and the remote device may provide certain advantages in some examples. An aircraft brake assembly may be exposed to relatively hostile environmental conditions (e.g., corrosive deicing fluids on a runway), and running wires to power to a wear measurement system mounted on the aircraft brake assembly may pose challenges. For example, the wires may be subject to the same hostile environmental conditions as the brake assembly, and may corrode or otherwise wear relatively fast, thereby decreasing the useful life of the wear measurement system. The passive powering of the wear measurement system described herein may reduce the number of wires, if not eliminate all wire, connecting the wear measurement system to power sources, and, therefore, may be more robust and longer lasting than wired wear measurement systems.

The wear level of a brake disc stack may be determined using the devices, systems, and techniques herein without requiring a technician to manually push in a wear pin, visually inspect the wear pin and make a subjective determination as to wear level, and the like. Instead, the technician or other user may only need to walk around the landing gear with a remote device, interrogate each sensor system mounted on the aircraft brake assemblies with the remote device (e.g., by powering the sensor system via the remote device), and read or otherwise receive an amount of wear automatically determined by the sensor system or the remote device. In this way, the devices, systems, and techniques for determining an amount of wear of a brake disc stack assembly may decrease turn around time for determining the wear amount compared to other proposed systems.

Existing brake disc stack wear measurement devices, systems, and techniques may also not record, collect, or display the measurement data in a meaningful way. In contrast, in some examples described herein, brake disc stack wear measurements for a particular brake assembly may be stored, e.g., which may enable patterns of wear to be determined, and for replacement parts to be ordered. The preordering of replacement parts may help reduce the amount of time the aircraft (or other vehicle) is out of commission for maintenance purposes.

While aircraft brake assemblies are primarily referred to herein for ease of description, the example brake disc stack wear measurement devices, systems, and techniques described herein may be used with brake assemblies of other vehicles, the brake assemblies including a brake disc stack the wears with brake usage.

FIG. 1 is a schematic diagram illustrating an example aircraft brake assembly that includes a wear measurement system, in accordance with one or more examples described herein. In the example shown in FIG. 1, aircraft brake assembly 10 includes wheel 12, actuator assembly 14, brake disc stack 16, and axle 18. Wheel 12 includes wheel hub 20, wheel outrigger flange 22, lug bolt 26, and lug nut 28. Actuator assembly 14 comprises actuator housing 30, actuator housing bolt 32, and a plurality of pistons (not labeled). Wheel outrigger flange 22 is mechanically affixed to wheel hub 20 by lug bolts 26 and lug nuts 28. During assembly, an inflatable tire (not shown) may be placed over wheel hub 20 and secured on an opposite side by wheel outrigger flange 22. Thereafter, lug nuts 28 can be tightened on lug bolts 26, and the inflatable tire can be inflated.

Assembly 10 may be mounted to an aircraft via torque tube 42 and axle 18. In the example of FIG. 1, torque tube 42 is affixed to axle 18 by a plurality of bolts 46. Torque tube 42 supports actuator assembly 14 and stators 38 of brake disc stack 16. Axle 18 may be mounted on a strut of a landing gear (not shown) to connect the assembly 10 to an aircraft. During operation of the aircraft, braking may be necessary from time to time, such as during landing and taxiing. Accordingly, aircraft brake assembly 10 may support braking through actuator assembly 14 and brake disc stack 16. During operation, pistons of actuator assembly 14 may extend away from actuator housing 30 to axially compress brake disc stack 16 against compression point 48 to provide braking.

Brake disc stack 16 includes alternating rotor discs 36 and stator discs 38. Rotor discs 36 are mounted to wheel 12, and in particular wheel hub 20, by beam keys 40. Stator discs are mounted to axle 18, and in particular torque tube 42, by splines 44. In the example of FIG. 1, brake disc stack 16 includes four rotors 36 and five stators 38. However, a different number of rotors and/or stators may be included in brake disc stack 16. Further, the relative positions of the rotors and stators may be reverse, e.g., such that rotor discs 36 are mounted to torque tube 42 and stator discs 38 are mounted to wheel hub 20.

Rotor discs 36 and stator discs 38 may be mounted in assembly 10 by beam keys 40 and splines 44, respectively.

Beam keys 40 may be circumferentially spaced about an inner portion of wheel hub 20. Beam keys 40 may be shaped with opposing ends (e.g., opposite sides of a rectangular) and may have one end mechanically affixed to an inner portion of wheel hub 20 and an opposite end mechanically affixed to an outer portion of wheel hub 20. Beam keys 40 may be integrally formed with wheel hub 20 or may be separate from and mechanically affixed to wheel hub 20, e.g., to provide a thermal barrier between rotor discs 36 and wheel hub 20.

Splines 44 may be circumferentially spaced about an outer portion of torque tube 42. Splines 44 may be integrally formed with torque tube 42 or may be separate from and mechanically affixed to torque tube 42. In some examples, splines 44 may define lateral grooves in torque tube 42. As such, stator discs 38 may include a plurality of radially inwardly disposed notches configured to be inserted into a spline.

Brake assembly 10 includes a wear measurement system, which, in the example shown in FIG. 1, includes wear pin 50, emitter 52, sensor system 54, and remote device 56. As described in further detail with respect to FIG. 2, emitter 52 is configured to emit a signal and a sensor of sensor system 54 may be configured to generate an output indicative of a characteristic of the signal, such as the signal strength. Sensor system 54 may further comprise a controller configured to receive the output generated by the sensor, and wirelessly transmit an indication of the characteristic of the signal (determined based on the sensor output) to remote device 56. In some examples, the controller of sensor system 54 or a processor of remote device 56 may determine an amount of wear of brake disc stack 16 (e.g., relative to a predetermined state in which stack 16 was less worn) based on the indication of the characteristic of the signal. The indication can be, for example, a value or other parameter that varies as a function of the characteristic of the signal. For example, the indication can be the raw output from sensor 113 or a value determined based on the raw output.

In the example shown in FIG. 1, sensor system 54 and emitter 52 are selected to be robust and suitable for use in the relatively harsh operating environment of brake assembly 10. For example, the components of sensor system 54 and emitter 52 may be selected to be able to operate in environments up to 300 degrees Fahrenheit (about 150 degrees Celsius), as well as in environments that may be subject to ice, shock, and vibration.

As shown in FIG. 1, remote device 56 is configured to transmit electromagnetic energy or the like that passively powers sensor system 54. When powered, sensor system 54 may transmit an indication of the characteristic of the signal sensed by sensor 113 to remote device 56. In this way, remote device 56 may wirelessly power sensor system 54, such that sensor system 54 may not include a power source (e.g., a battery) and may not be connected to a power source, e.g., via wires running through brake assembly 10. Likewise, in some examples, remote device 56 may wirelessly power emitter 52.

FIG. 1 illustrates an example brake assembly 10. In other examples, the wear measurement system described herein may be used with other brake assemblies having other configurations.

Figure 2:
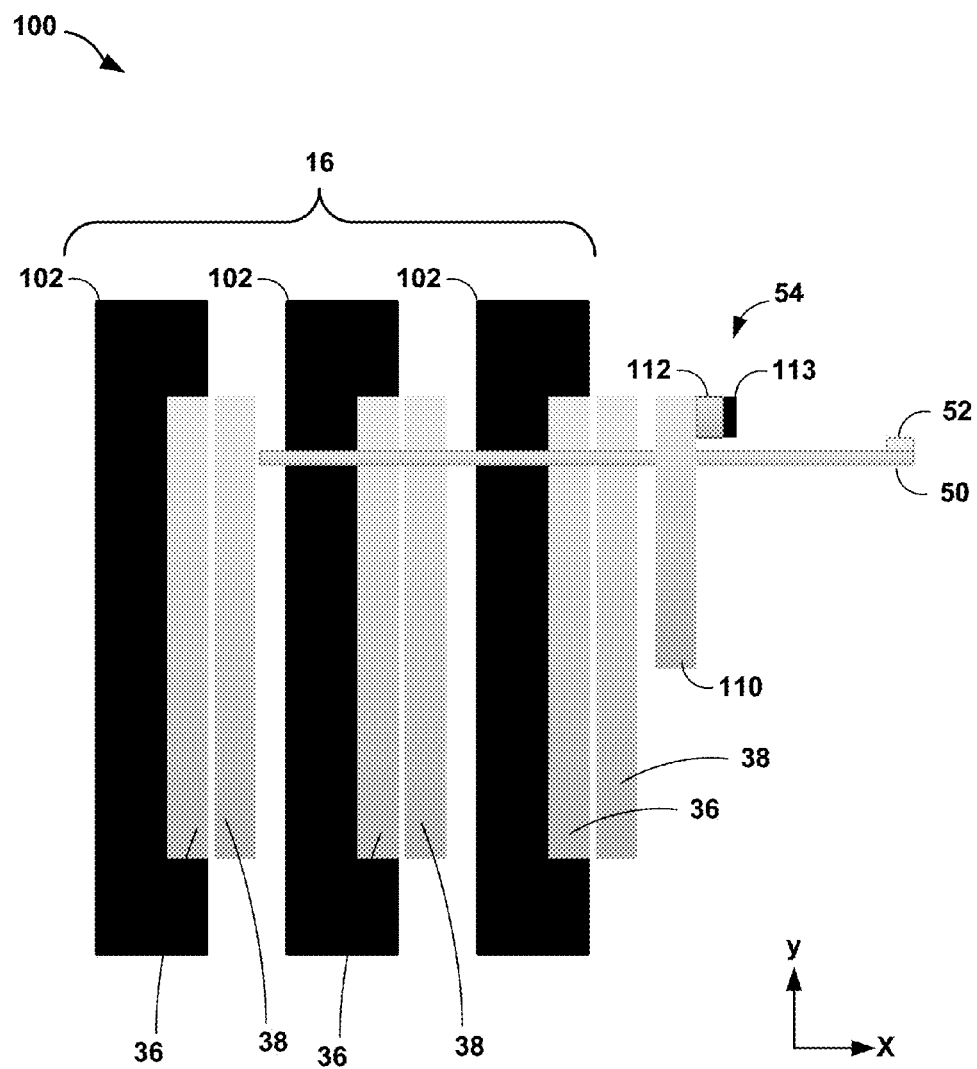
FIG. 2 is a conceptual diagram illustrating an example wear measurement system.

FIG. 2 is a block diagram illustrating brake disc stack 16, an example wear measurement system 100, bracket 110 of brake assembly 10, and wear pin 50. In the example shown in FIG. 2, wear measurement system 100 includes bracket 110, emitter 52, and sensor system 54 including controller 112 and sensor 113. Brake disc stack 16 includes rotors 36, stators 38, and mounting brackets 102. As the individual rotors 36 and stators 38 of brake disc stack 16 wear over time, the dimension of brake disc stack 16 may decrease in the x-dimension (orthogonal x-y axes are shown are in FIG. 2 for ease of description only and do not indicate any particular orientation of brake disc stack 16 in space). Wear pin 50 may be coupled to any suitable portion of brake disc stack 16, such as a pressure plate (e.g., as defined by stator 38 on the end closest to bracket 110), rotor 36, or stator 38, such that as brake disc stack 16 wears, wear pin moves relative to bracket 110.

Bracket 110 may be coupled to any suitable portion of the aircraft (e.g., landing gear assembly) and does not move in the x-direction as brake disc stack 16 wears.

In some examples, emitter 52 and at least sensor 113 of sensor system 54 are configured to move relative to each other (e.g., away from or closer to each other) as brake stack 16 wears. As shown in FIG. 2, in one example, emitter 52 may be mechanically connected to wear pin 50 (e.g., an end of wear pin 50 furthest from brake disc stack 16 or any other suitable location along wear pin 50) and sensor system 54 may be mechanically connected to bracket 110. However, in other examples, sensor system 54 may be mechanically connected to wear pin 50 and emitter 52 is mechanically connected to bracket 110. In addition, in the example shown in FIG. 2, emitter 52 and sensor 113 are configured to move towards each other as brake disc stack 16 wears. In particular, emitter 52 is configured to move towards a stationary sensor 112. In other examples, as described with respect to FIG. 3, the wear measurement system can be configured such that emitter 52 and sensor 113 are configured to move away from each other as brake disc stack 16 wears.

Emitter 52 includes any suitable apparatus configured to emit a signal that can be sensed by sensor system 54, where a characteristic of the signal sensed by sensor 113 changes as a function of a relative distance between emitter 52 and sensor 113. Thus, emitter 52 and sensor 113 are configured such that a characteristic of the signal output by emitter 52 and sensed by sensor 113 indicates a distance between emitter 52 and sensor 113. For example, in some examples, emitter 52 includes a magnet that emits a magnetic field, and sensor 113 may include a magnetic field strength sensor, such as a magnetometer (e.g., a multi-axis magnetometer), Hall-effect sensor, or the like. In other examples, emitter 52 includes an optical emitter (e.g., a laser) and sensor 113 may include an optical sensor. In other examples, emitter 52 includes an acoustic emitter and sensor 113 may include an acoustic sensor; a beat frequency of a signal received by sensor 113 may indicate the relative distance between emitter 52 and sensor 113, which may indicate the level of wear of brake disc stack 16. Controller 112 may output a signal indicative of the beat frequency.

As another example, emitter 52 includes a radiofrequency signal emitter (or another electrical signal emitter) and sensor 113 may include a radio transceiver. For example, sensor 113 can include two antennas placed at a known distance apart (e.g., half a wavelength apart), and a controller of system 54 can determine the phase difference between signals sensed by the two or more antennas of sensor 113 in order to determine the relative distance between emitter 52 and sensor 113, which may indicate the level of wear of brake disc stack 16. Controller 112, a processor of external device 56, or another processor can be configured to receive the phase difference, and determine the relative distance between emitter 52 and sensor 113 based on the determined phase difference. For example, controller 112, the processor of device 56, or another processor can stored information that associate different phase differences with respective different levels of brake disc stack wear. The information can be stored by, for example, a memory of controller 112, device 56, or another device As another example, emitter 52 include a capacitive plate (to which power can be passively applied by remote device 56) and a controller 112 can be configured to output a signal indicative of the capacitance between emitter 52 and sensor 113. Controller 112, a processor of external device 56, or another processor can be configured to receive the determined capacitance, and determine the relative distance between emitter 52 and sensor 113, which may indicate the level of wear of brake disc stack 16, based on the determined capacitance. For example, controller 112, the processor of device 56, or another processor can stored information that associate different capacitance values with respective different levels of brake disc stack wear. The information can be stored by, for example, a memory of controller 112, device 56, or another device. A processor may receive the signal output by controller 112, determine a capacitance value based on a characteristic of the signal (e.g., an amplitude or frequency of the signal), compare the determined capacitance value to stored information, and, based on the comparison, determine the brake disc stack wear based on the wear level associated with the determined capacitance value.

Figure 4:
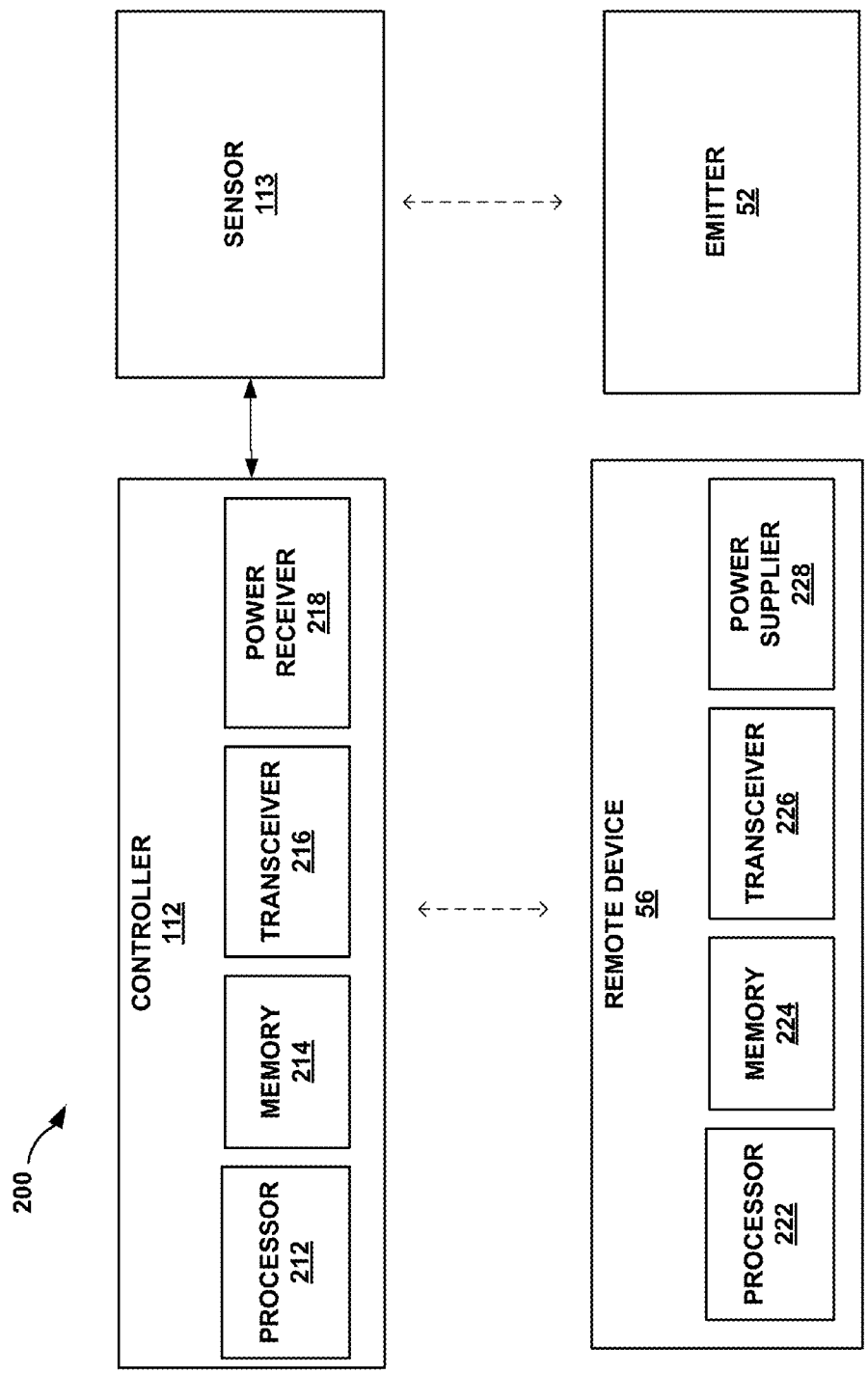
FIG. 4 is a block diagram illustrating an example wear measurement system.

As described with respect to FIG. 4, controller 112 may include a processor and memory. The processor, as well as other processors described in this disclosure, may include one or more digital signal processors (DSPs), general purpose microprocessors, application specific integrated circuits (ASICs), field programmable logic arrays (FPGAs), or other equivalent integrated or discrete logic circuitry, or combinations thereof. The functions attributed to the controllers and processors described herein may be provided by a hardware device and embodied as software, firmware, hardware, or any combination thereof.

In some examples, controller 112 may include a transceiver configured to send and receive data via any suitable wireless communication technique, such as, but not limited to, WiFi, Bluetooth, infrared, or radiofrequency techniques (e.g., according to the ISO 18000-2 and ISO 14443A standards). Controller 112 may be passively powered by an external device 56. For example, controller 112 may be inductively powered by external device 56 (also referred to as a remote device). Using a passively powered controller 112 may reduce the need to perform maintenance on controller 112 because there may not be a need to run wires, or install or replace an internal power source of controller 112. Likewise, replacing the entire controller 112 may be easier because the number of connections between controller 112 and the aircraft may be reduced or eliminated.

In operation, in some examples, emitter 52 may be configured to emit a magnetic field (or other signal) and sensor 113 may be configured to sense the magnetic field and generate an output indicative of a characteristic of the magnetic field (e.g., a strength of the magnetic field). Sensor 113 may be configured to convert the electromagnetic energy of the magnetic field into a signal that can be read by controller 112. For example, sensor 113 may detect the magnetic field emitted by emitter 52 and produce a voltage proportional to the strength of the magnetic field detected at sensor 113.

In some examples, emitter 52 may include an optical emitter such as a laser configured to emit a laser beam. Sensor 113 may be configured to sense the laser beam and generate an output indicative of a characteristic of the laser beam (e.g., the time it takes the beam to travel between emitter 52 and sensor 113). Optical emitter 52 and sensor 113 may be mechanically connected to opposing structures (e.g., bracket 110 and wear pin 50) so that emitter 52 and sensor 113 move relative to each other as brake stack wears. However, in some examples, optical emitter 52 and sensor 113 may be mechanically connected to the same structure (e.g., wear pin 50), such that, where optical emitter 52 emits a laser beam, the beam may reflect off another structure (e.g., bracket 110) and sensor 113 may detect the reflected beam. Sensor 113 may be configured to output a signal indicative of the characteristic of the emitted signal and controller 112 may receive the signal output by sensor 113. For example, emitter 52 may emit a laser beam, sensor 113 may detect the laser beam and determine the time that elapsed between when the beam was emitted and when the beam was detected, and sensor 113 may output a signal indicative of the elapsed time.

In some examples, emitter 52 may include two antennas that may be configured to emit radio frequencies (e.g., two different frequencies). Sensor 113 may be configured to detect the frequencies and measure the phase or beat frequency of the emitted frequencies. Sensor 113 may output a signal indicative of the detected frequencies such that the signal may be read by controller 112.

Sensor 113 may be configured to continuously sense the signal output by emitter 52 or detect the signal at regular or irregular periodic intervals (e.g., once per day, after every landing, and the like). In some examples, sensor 113 may be configured to generate the output indicative of the characteristic of the signal on demand, such as when a field technician performs an inspection using remote device 56 and wirelessly interrogates sensor system 54 by wirelessly providing power to controller 112. Sensor 113 may be configured to sense the signal output by emitter 52 and generate an output indicative of the sensed signal only when brake disc stack 16 is compressed or only when brake disc stack 16 is uncompressed.

In some examples, controller 112 may receive a signal from sensor 113 shortly after being powered-up via the energy emitted by external device 56. For example, sensor 113 may detect a magnetic field and produce a voltage (or another suitable output), and controller 112 may receive the voltage from sensor 113 immediately upon power-up.

In some examples, emitter 52 and sensor 113 may both be wirelessly powered via external device 56. In some instances, powering emitter 52 and sensor 113 via the same wireless power source may provide resilience to interference, e.g., compared to examples in which emitter 52 passively emits a magnetic field. In addition, wirelessly powering both emitter 52 and sensor 113 may help maintain the calibration between emitter 52 and sensor 113. In some examples, wirelessly powering both emitter 52 and sensor 113 may also provide a facility for radiofrequency (RF) transmission techniques, such as modulated codes and identifiers, to be employed by emitter 52.

Brake disc stack 16 may become worn due to friction between rotors 36 and stators 38. As brake disc stack 16 wears, wear pin 50 may move relative to bracket 110. One of sensor 113 or emitter 52 is coupled to wear pin 108, such that one of sensor 113 or emitter 52 moves with wear pin 50 as brake disc stack 16 wears. In this way, emitter 52 and sensor 113 may be configured to move relative to one another (e.g., emitter 52 may be coupled to wear pin 108 and sensor 113 may be coupled to bracket 110, or vice versa). In the example shown in FIG. 2, emitter 52 may be coupled to the end of wear pin 50 furthest from brake disc stack 16. In this example, as brake disc stack 16 wears down, wear pin 50 and emitter 52 move towards bracket 110 (e.g., to the left in FIG. 2).

As emitter 52 and sensor 113 move relative to each other, thereby changing a distance between emitter 52 and sensor 113 (when the brake assembly is in a resting state or a compressed state), a characteristic of the signal (e.g., the strength of a magnetic field, or time elapsed between when a laser beam was emitted and when it was sensed) generated by emitter 52 and sensed by sensor 113 may change. Thus, the characteristic of the signal may change as a function of the amount of wear of brake disc stack 16 and may be used by controller 112 or remote device 56, or both, to determine the amount of wear of brake disc stack 16. In the example shown in FIG. 2, emitter 52 moves towards bracket 110 as brake disc stack 16 wears, such that, if emitter 52 is a magnet, the magnetic field at sensor 113 becomes stronger as brake disc stack 16 wears.

In other examples, emitter 52 may be coupled to wear pin 50 between bracket 110 and brake disc stack 16. In these examples, as brake disc stack 16 wears, emitter 52 moves away from bracket 110 (e.g., to the left in FIG. 2), such that, if emitter 52 is a magnet, the magnetic field at sensor 113 becomes weaker as brake disc stack 16 wears.

Regardless of whether sensor 113 and emitter 52 move towards or away from each other as brake disc stack 16 wears, sensor 113 is configured to sense the signal output by emitter 52 and generate an output indicative of a characteristic of the signal. For example, if emitter 52 is a magnet, sensor 113 may output a voltage proportional to the strength of the magnetic field at sensor 113.

In some examples, controller 112, remote device 56, or another device may determine an amount of wear of brake disc stack 16 based on the output generated by sensor 113. The amount of wear of brake disc stack 16 can be any suitable parameter indicative of the state of wear of brake disc stack 16. For example, in some examples, the amount of wear of brake disc stack 16 is a measurement of the amount (e.g., a distance) brake disc stack 16 has worn in the x-axis direction relative to a predetermined baseline. The predetermined baseline can be stored by controller 112, remote device 56, or another device, and can be, for example, a starting measurement (in dimensions of length) when the brake disc stack 16 was installed or any other prior measurement.

In some examples, controller 112, remote device 56, or another device may receive the output generated by sensor 113 (e.g., a voltage) and determine a distance between emitter 52 and sensor 113 based on the output. The distance may increase or decrease (depending on the particular configuration of the wear measurement system) as brake disc stack 16 wears. A characteristic of the signal received by sensor 113 (e.g., the strength of the magnetic field) may correspond to a distance between emitter 52 and sensor 113. Likewise, the output from sensor 113 (e.g., a voltage) may be proportional to the signal received by sensor 113 (e.g., strength of the magnetic field). In some examples, emitter 52 includes a magnet and the strength of the magnetic field received by sensor 113 may be associated with a voltage level. For example, controller 112, remote device 56, or another device may store a table or other data structure that associates a plurality of different voltage levels with respective distances between emitter 52 and sensor 113. In some examples, controller 112, remote device 56, or another device may then determine the distance between emitter 52 and sensor 113 based on the voltage output by sensor 113 by determining the distance associated with the voltage in the data structure.

As another example, the amount of wear of brake disc stack 16 can be a percentage of usable life of brake disc stack 16 remaining. For example, where emitter 52 includes a magnet, a plurality of different percentages of remaining useable life of brake disc stack 16 may be associated with respective magnetic field characteristics in a memory of controller 112, remote device 56, or another device, such that once the magnetic field characteristic is determined, controller 112 or a processor of remote device 56 may determine the percentage of useable life of brake disc associated with the magnetic field characteristic can be determined.

In some examples, controller 112 may determine the remaining useable lifespan of brake disc stack 16 based on the determined distance between emitter 52 and sensor 113. In some examples, controller 112 or another device, such as remote device 56, may store a table or other data structure that associates different distances (or, in some examples, voltages generated by sensor 113) with different amounts of wear. Controller 112 or the other device may then determine an amount of wear (e.g., as indicated by percentage of a usable life remaining or used up) by determining the amount of wear associated with the output generated by sensor 113.

In other examples, controller 112 may merely output the voltage (or other electrical signal characteristic) generated by sensor 113 to external device 56, and a processor of external device 56 may determine an amount of wear of brake disc stack 16 based on the output generated by sensor 113 and transmitted by controller 112, e.g., using any of the techniques described above with respect to controller 112.

Figure 3:
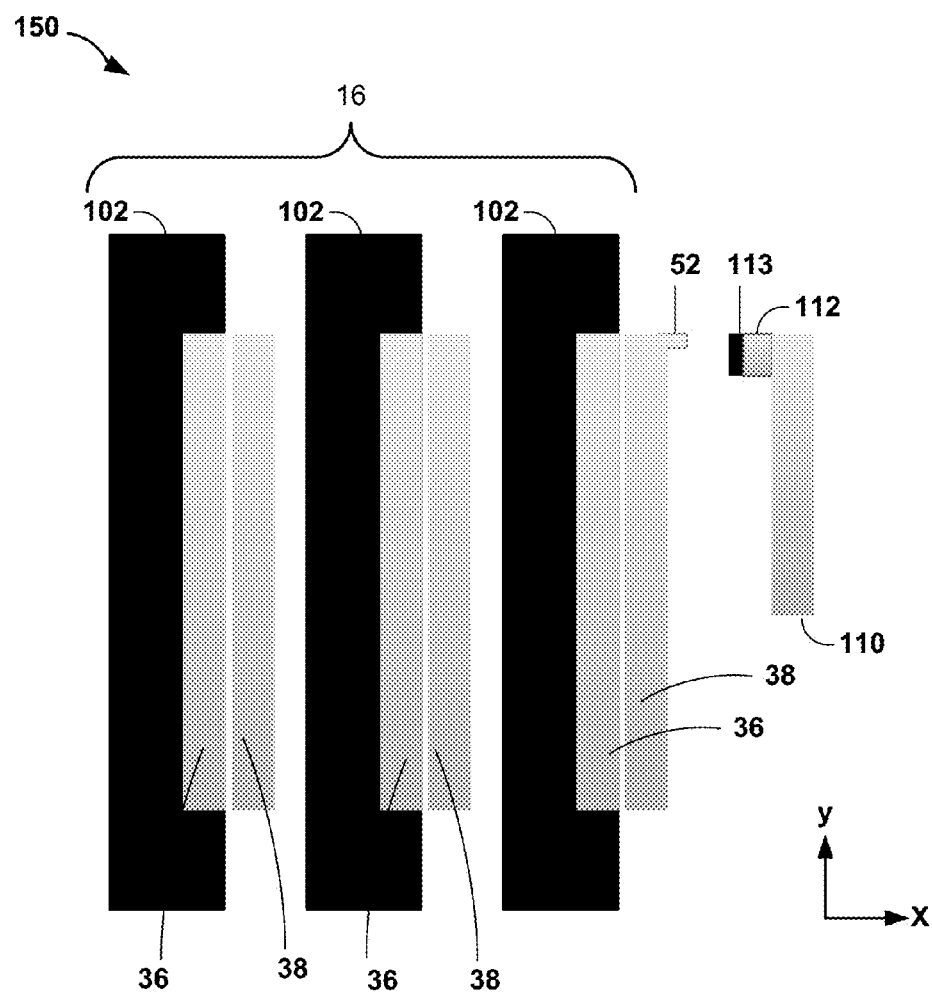
FIG. 3 is a conceptual diagram illustrating another example wear measurement system.

FIG. 3 is a block diagram illustrating another example wear measurement system 150, which is similar to wear measurement system 100 shown in FIG. 2, but shows a different placement of emitter 52, controller 112, and sensor 113. Instead of one of emitter 52 or sensor 113 being mechanically connected to wear pin 50 (shown in FIG. 2), in the example shown in FIG. 3, emitter 52 is mechanically connected to brake disc stack 16 and sensor 112 is mechanically connected to bracket 110. For example, emitter 52 can be connected to stator 38 at an end of stack 38, which may act as a pressure plate for brake disc stack 16 (against which an actuator applies a force to compress brake disc stack 16). In other examples, emitter 52 can be mechanically connected to bracket 110 and sensor 113 can be mechanically connected to brake disc stack 16.

A distance between a surface of brake disc stack 16 and bracket 110 may increase as rotors 36 and stators 38 are worn. Wear measurement system 150 is configured such that as brake disc stack 16 wears and decreases dimension in the negative x-axis direction (orthogonal x-y axes are shown in FIG. 3 for ease of description only), emitter 52 and sensor 112 move away from each other, rather than towards each other as in the example of wear measurement system 100 shown in FIG. 2. Accordingly, as brake disc stack 16 wears, emitter 52 may move away from sensor 113 such that a characteristic of the signal at sensor 113 changes as brake disc stack 16 wears. For example, where emitter 52 includes a magnet, emitter 52 may move away from sensor 113 such that magnetic field strength at sensor 113 decreases as brake disc stack 16 wears. In other examples, where emitter 52 includes an optical emitter (e.g., a laser), emitter 52 may move away from sensor 113 such that the time between when emitter 52 emits a signal (e.g., a laser beam) and when the signal is detected by sensor 113 may increase as brake disc stack 16 wears.

In some examples, emitter 52 and sensor 113 may both be mechanically connected to either bracket 110 or brake disc stack 16. For example, where emitter emits a laser beam, emitter 52 and sensor 113 may be mechanically connected to bracket 110 such that the laser beam reflects off brake disc stack 16 and the reflected beam is detected by sensor 113.

In some examples, controller 112, a processor of remote device 56, or another component of wear measurement system 150 may be configured to determine the amount of wear of brake disc stack 16 based on an output generated by sensor 113 using any of the techniques described above, e.g., with respect to FIG. 2.

FIG. 4 is a conceptual and block diagram illustrating an example wear measurement system 200, which can be an example of system 100 of FIG. 2 or system 150 of FIG. 3. Wear management system 200 may include controller 112, sensor 113, emitter 52, and remote device 56.

In the example shown in FIG. 4, controller 112 includes processor 212, memory 214, transceiver 216, and power receiver 218. Transceiver 216 is configured to support wireless communication between controller 112 and an external device, such as remote device 56. In some examples, processor 212 may transmit information indicative of a characteristic of a signal sensed by sensor 113 (e.g., raw sensor outputs or parameterized sensor output) to remote device 56. In addition to, or instead of the sensor outputs, processor 212 may determine an amount of brake disc stack 16 wear determined based on an output of sensor 113 and transmit the determined amount of brake disc stack 16 wear to remote device 56 via transceiver. Processor 212 may also receive other information from remote device 56 or another device via transceiver 216, such as updates to software implemented by processor 212 to determine an amount of brake disc stack 16 wear or to make other determinations.

Power receiver 218 may include an antenna configured to receive inductive power generated by remote device 56. In addition, in some examples, power receiver 218 may include other components configured to convert the inductively received power into useful energy for powering controller 112, such as, but not limited to, one or more capacitors, one or more, rectifiers or one or more DC-DC charge pumps. Remote device 56 may include a power transmitter configured to generate and emit energy (e.g., electromagnetic waves) that induces a current in the antenna of power receiver 218. Thus, power receiver 218 enables controller 112 to be passively powered by electromagnetic induction, such that controller 112 does not include wires running to controller 112 from a power source or an internally housed power source. A passively powered controller 112 may make it easier to install, operate, and maintain wear measurement system 200. In addition, controller 112 that is passively powered and does not include an internal power source may be more compact relative to a controller that includes a power source. The more compact design may be easier to install in the relatively tight spaces available in an aircraft brake assembly.

In other examples, power receiver 218 may include a wired connection so that controller 112 may be powered using batteries or wires.

Once controller 112 is powered by the energy emitted by remote device 56, processor 212 may control transceiver 216 to transmit an indication of a characteristic of a signal sensed by sensor 113. This may be, for example, a real-time sensor output, at the time controller 112 is powered. For example, processor 212 may control transceiver 216 to transmit a raw electrical signal output by sensor 113 or a parameterized signal (e.g., a voltage level determined based on the raw electrical signal output by sensor 113). In this way, remote device 56 may be configured to interrogate sensor system 54 by transmitting energy that powers controller 112 and causes controller 112 to transmit an indication of a characteristic of a signal sensed by sensor 113.

In some examples, remote device 56 may include processor 222, memory 224, transceiver 226, and power supplier 228. In some examples, remote device 56 may is a handheld device, such as mobile computing device (e.g., smartphone, tablet, and the like). A handheld device may permit device 56 to be relatively portable, which may increase the usefulness of wear measurement system 200 in the field, e.g., during a regular aircraft maintenance event.

Transceiver 216 is configured to support wireless communication between remote device 56 and controller 112. Power supplier 228 is configured to generate and emit energy (e.g., electromagnetic waves) that power controller 112. Power supplier 228 may provide power to controller 112 without using cables or wires, for example, using inductive power to emit an electromagnetic field that may be received by the power receiver 218 of controller 112.

In operation, emitter 52 may emit a signal (e.g., a magnetic field) that is sensed by sensor 113. Controller 112 may be passively powered by remote device 56 when an amount of wear of brake disc stack 16 is desired. For example, a technician may position remote device 56 proximate to controller 116 and control device 56 to emit electromagnetic energy to power controller 112. The energy may energize power receiver 218 of controller 112 and cause controller 112 to activate. In some examples, power supplier 228 is configured to generate a 824 megahertz (MHz) to about 960 MHz signal having a power of about 8 Decibel-milliwatts (dBm) to about 17 dBm, which may enable power receiver 218 to charge within one second of being exposed to the signal if device 56 is held within one meter of power receiver 218, or within 100 seconds if device 56 is held 10 meters from power receiver 218.

When activated, processor 212 may receive an output generated by sensor 113, where the output varies as a function of a characteristic of the signal emitted by emitter 52. For example, sensor 113 may generate an output (e.g., a voltage) that indicates a characteristic of a signal (e.g., the strength of a magnetic field) emitted by emitter 52. When powered, controller 112 may receive the output from sensor 113 and, in some examples, may transmit an indication of the output (e.g., the raw output itself or a parameterized output, such as a magnitude of the voltage) to remote device 56 via the respective transceivers 216, 226. In some examples, processor 212, processor 222, or both processors 212, 222 determine an amount of wear of brake disc stack 16 based on the output generated by sensor 113.

As discussed above, the voltage output (or other output) generated by sensor 113 may be proportional to a characteristic of the signal (e.g., the magnetic field strength) sensed by sensor 113, which may itself be proportional to the distance between emitter 52 and sensor 113. The distance between emitter 52 and sensor 113 may be proportional to the amount of wear of the brake disc stack 16.

Processor 222 may store the information received from controller 112 in memory 224. The information can include, for example, sensor outputs, determined amounts of brake disc stack 16 wear, and the like. In addition, in examples in which processor 222 determines an amount of brake disc stake 16 wear, processor 222 may store the determined amounts in memory 224. As described above, in some examples, the amount of brake disc stack wear can be any suitable quantification of wear, such as, but not limited to, a magnitude of wear (e.g., measured in units of length) relative to a predetermined baseline, the remaining useable lifespan of brake disc stack 16 as a percentage of wear or a magnitude remaining, or any combination thereof.

In some examples, processor 222 may be configured to determine whether the amount of wear determined based on the output of sensor 113 indicates maintenance of brake assembly 10 is advisable. For example, in response to determining the amount of brake disc stack 16 wear is less than or equal to a threshold value (stored by memory 224), processor 222 may generate a notification to a user. The notification may indicate, for example, that a particular wear level was detected (e.g., less than 25% of useful brake disc stack 16 life is remaining) The notification can be, for example, a visual notification (e.g., presented via a display or other visual indicator, such as activation of a light, of remote device 56), an audible notification, or a somatosensory notification (e.g., the handheld device may vibrate to provide the notification). In response to receiving the notification, the user may perform any desired maintenance, such as replacement of one or more rotors 36 or stators 38.

In some examples, processor 222 may store a plurality of determined amounts of brake disc stack 16 wear in memory 224, each amount being measured at a different time, and associate the determined amounts of wear with the particular brake assembly 10 in memory 224. In some examples, remote device 56 may also upload the values to a remote database via transceiver 226 or another communications module. Another device may then access historical wear information, which may be useful for analyzing the wear pattern of brake assembly 10, the wear pattern of brakes for a particular aircraft, a particular type of aircraft, a particular type of brake assembly, and the like.

In some examples, processor 222 may be configured to predict when one or more rotors 36 or stators 38 may need to be replaced based on the output of sensor 113. For example, based on historical wear data for the particular brake assembly 10, processor 222 may determine the rate of wear of brake disc stack 16 and predict the number of landings until the amount of wear is less than or equal to a predetermined threshold wear level. In this way, wear measurement system 200 may not only be used to obtain real-time brake disc stack 16 measurements, but may also be used to plan brake assembly 10 maintenance. This may improve the maintenance scheduling and workflow by allowing an entity (e.g., a maintenance facility) to anticipate when brake disc stack 16 will need to be replaced and have parts readily available.

Memory 214 and memory 222, as well as other memories described herein, may include any one or more volatile or non-volatile media, such as a random access memory (RAM), read only memory (ROM), non-volatile RAM (NVRAM), electrically erasable programmable ROM (EEPROM), flash memory, and the like. Memories 214, 222 may store computer-readable instructions that, when executed by the respective processors 212, 222 cause controller 112 and remote device 56, respectively, to perform various functions described herein.

Figure 5:
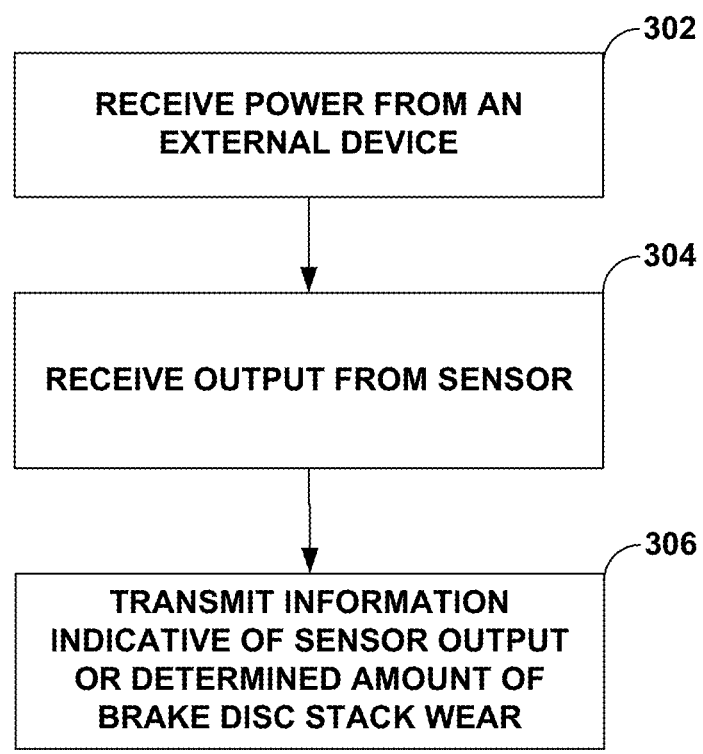
FIG. 5 is a flow diagram illustrating an example method of measuring an amount of wear of a brake disc stack of a brake assembly using a measurement system.

FIG. 5 is a flow diagram illustrating an example method of determining an amount of wear of a brake disc stack of a brake assembly. For purposes of illustration only, the example method will be described with reference to brake assembly 10 and the wear measurement system described in FIG. 4. However, the method may apply to other wear measurement systems.

In some examples, power supplier 228 of remote device 56 may wirelessly transmit power to controller 112, which may wirelessly receive the power from remote device 56 via power receiver 218 (302). Processor 222 may receive an output from sensor 113 (304), which is configured to sense a signal (e.g., a magnetic field) emitted by from emitter 52 and generate an output indicative of a characteristic of the sensed signal. For example, sensor 113 may sense a magnetic field and output a voltage proportional to the strength of the magnetic field. Processor 212 of controller 112 may receive the signal output by sensor 113 and control transceiver 216 to transmit information indicative of the sensor output or a determined level of brake disc stack 16 wear to remote device 56 (306). In some examples, processor 212 receives the output from sensor 113, determines a voltage value based on the signal (e.g., the magnitude of the voltage), and transmits the voltage value to remote device 56.

Processor 212 of controller 112 or processor 222 of remote device 56 may determine the amount of wear of brake disc stack 16 based on output generated by sensor 113 using any of the techniques described above.

The techniques of this disclosure may be implemented in a wide variety of computing devices. Any components, modules or units have been described provided to emphasize functional aspects and does not necessarily require realization by different hardware units. The techniques described herein may be implemented in hardware, software, firmware, or any combination thereof. Any features described as modules, units or components may be implemented together in an integrated logic device or separately as discrete but interoperable logic devices. In some cases, various features may be implemented as an integrated circuit device, such as an integrated circuit chip or chipset.

As mentioned above, the techniques of this disclosure may also be implemented on an article of manufacture comprising a computer-readable storage medium. The term "processor," as used herein may refer to any of the foregoing structure or any other structure suitable for implementation of the techniques described herein. In addition, in some aspects, the functionality described herein may be provided within dedicated software modules or hardware modules configured for performing the techniques of this disclosure. Even if implemented in software, the techniques may use hardware such as a processor to execute the software, and a memory to store the software. In any such cases, the devices described herein may define a specific machine that is capable of executing the specific functions described herein. Also, the techniques could be fully implemented in one or more circuits or logic elements, which could also be considered a processor.

Various examples have been described. These and other examples are within the scope of the following claims.

What is claimed is:

1. A system comprising:
a brake disc stack;
an emitter configured to emit a signal;
a sensor configured to sense the emitted signal, generate an output indicative of a characteristic of the sensed signal, wherein the sensor and the emitter are configured to move relative to each other as the brake disk stack wears;
a passively powered controller operatively coupled to the sensor and configured to:
wirelessly receive power from a remote device, and receive the output generated by the sensor; and a processor configured to determine an amount of wear of the brake disc stack based on the output generated by the sensor, wherein the controller is configured to transmit, to the remote device, at least one of: information indicative of the output generated by the sensor or the amount of wear of the brake disc stack determined based on the output.

2. The system of claim 1, further comprising a wear pin configured to move in a first direction with the brake disc stack as the brake disc stack wears, wherein one of the sensor or the emitter are mechanically coupled to the wear pin.

3. The system of claim 1, wherein one of the sensor or the emitter are mechanically coupled to the brake disc stack and configured to move away from the other of the sensor or the emitter as the brake disc stack wears.

4. The system of claim 1, wherein the emitter comprises a magnet and the signal emitted by the emitter includes a magnetic field, wherein the output is indicative of the strength of the magnetic field.

5. The system of claim 1, wherein the emitter comprises at least one of: an optical emitter, an acoustic emitter, a radiofrequency signal emitter, or a capacitive plate.

6. The system of claim 1, wherein the processor is configured to determine a distance between the emitter and the sensor based on the output generated by the sensor, the distance between the emitter and the sensor indicating the amount of brake wear.

7. The system of claim 1, wherein the processor is configured to compare the amount of wear to a threshold value and generate a notification in response to determining the amount is less than or equal to the threshold value.

8. The system of claim 1, wherein the processor is configured to determine a percentage of useful life remaining of the brake disc stack based on the output generated by the sensor, the percentage of useful life remaining indicating the amount of brake wear.

9. The system of claim 1, further comprising the remote device, wherein the remote device comprises the processor.

10. The system of claim 1, wherein the controller comprises the processor.

11. The system of claim 1, further comprising a data storage device comprising:
a data structure including values associated with the output generated by the sensor and values indicating the amount of brake wear,
wherein the processor is further configured to determine the amount of wear of the brake disc stack based on the output generated by the sensor by determining a value associated with the output generated by the sensor in the data structure and determining a value indicating the amount of brake wear that corresponds to the value associated with the output generated by the sensor.

12. The system of claim 11, wherein the output generated by the sensor includes a voltage, wherein the data structure includes a mapping table that maps voltage to the amount of brake wear in the brake disc stack, wherein the processor is configured to determine the amount of brake wear in the brake disc stack by comparing the amount of voltage output by the sensor to the mapping table and determining a corresponding value in the mapping table indicating the amount of brake wear.

13. A method comprising:
emitting, by an emitter, a signal;
detecting, by a sensor, the signal emitted by the emitter;
generating, by the sensor, an output indicative of a characteristic of the signal emitted by the emitter;
wirelessly receiving, by a passively powered controller, power from a remote device;
receiving, by the passively powered controller, the output generated by the sensor; and
determining an amount of wear of a brake disc stack based on the output generated by the sensor.

14. The method of claim 13, further comprising:
transmitting, to the remote device, at least one of: information indicative of the output generated by the sensor or the amount of wear of the brake disc stack determined based on the output.

15. The method of claim 13, further comprising:
determining a distance between the emitter and the sensor based on the output generated by the sensor, wherein the distance between the emitter and the sensor indicates a the amount of brake wear.

16. The method of claim 13, further comprising:
comparing, by a processor, the amount of brake wear to a threshold value;
determining, by the processor, whether the amount of break wear is less than or equal to the threshold value; and
generating a notification in response to determining the amount of break wear is less than or equal to the threshold value.

17. The method of claim 13, further comprising:
determining, by the processor, a percentage of useful life remaining of the brake disc stack based on the output generated by the sensor, wherein the percentage of useful life remaining indicates the amount of brake wear.

18. The method of claim 13, wherein the emitter comprises a magnet and the signal emitted by the emitter includes a magnetic field, and wherein output is indicative of the strength of the magnetic field.

19. A system comprising:
means for emitting a signal;
means for sensing the signal emitted by the emitter and generating an output indicative of a characteristic of the signal sensed by the means for sensing;
means for wirelessly receiving power from a remote device to power the means for sensing the signal and generating the output; and
means for determining an amount of wear of a brake disc stack based on the output.

20. The system of claim 19, wherein the signal includes a magnetic field, and wherein output is indicative of the strength of the magnetic field.

* * * * *